(12) United States Patent
Kim et al.

(10) Patent No.: US 11,517,748 B2
(45) Date of Patent: Dec. 6, 2022

(54) WOUND TREATMENT PATCH USING STATIC ELECTRICITY AND METHOD FOR FABRICATING THE PATCH

(71) Applicant: RESEARCH & BUSINESS FOUNDATION SUNGKYUNKWAN UNIVERSITY, Suwon-si (KR)

(72) Inventors: SangWoo Kim, Yongin-si (KR); Byung Ok Choi, Seoul (KR); Hyoung Taek Kim, Suwon-si (KR); Min Ki Kang, Suwon-si (KR); Young Jun Kim, Daejeon (KR); Han Yup Yum, Suwon-si (KR); Woo Seok Kang, Suwon-si (KR)

(73) Assignee: STATIC ELECTRICITY MEDICAL SOLUTIONS CORP., Suwon-si (KR)

( * ) Notice: Subject to any disclaimer, the term of this patent is extended or adjusted under 35 U.S.C. 154(b) by 0 days.

(21) Appl. No.: 17/110,673

(22) Filed: Dec. 3, 2020

(65) Prior Publication Data

US 2022/0176112 A1     Jun. 9, 2022

(30) Foreign Application Priority Data

May 13, 2020     (KR) .................. 10-2020-0056913

(51) Int. Cl.
| | |
|---|---|
| *A61N 1/04* | (2006.01) |
| *H05K 1/09* | (2006.01) |
| *B29C 39/12* | (2006.01) |
| *A61N 1/10* | (2006.01) |
| *B29L 31/00* | (2006.01) |
| *B29K 105/00* | (2006.01) |

(52) U.S. Cl.
CPC .............. *A61N 1/10* (2013.01); *A61N 1/0468* (2013.01); *A61N 1/0496* (2013.01); *B29C 39/123* (2013.01); *H05K 1/09* (2013.01); *B29K 2105/0061* (2013.01); *B29L 2031/753* (2013.01)

(58) Field of Classification Search
CPC ...... A61N 1/10; A61N 1/0496; A61N 1/0468; B29C 39/123
See application file for complete search history.

(56) References Cited

U.S. PATENT DOCUMENTS

| | | | |
|---|---|---|---|
| 7,945,302 B2* | 5/2011 | McAdams | A61N 1/044 600/382 |
| 2020/0061379 A1* | 2/2020 | Bogie | A61B 5/0531 |
| 2020/0316366 A1* | 10/2020 | Wang | A61N 1/0492 |
| 2021/0290944 A1* | 9/2021 | Hong | A61N 1/10 |

FOREIGN PATENT DOCUMENTS

| | | | | |
|---|---|---|---|---|
| WO | WO 2009/131738 A2 | 10/2009 | | |
| WO | WO-2020122668 A2 * | 6/2020 | | A61C 19/06 |

* cited by examiner

*Primary Examiner* — Unsu Jung
*Assistant Examiner* — Adreanne A. Arnold
(74) *Attorney, Agent, or Firm* — NSIP Law

(57) ABSTRACT

Disclosed are a wound treatment patch using static electricity, and a method for fabricating the wound treatment patch using static electricity. The patch includes a substrate made of a sticky polymer; a first electrode disposed in a first partial region of one face of the substrate and exposed to an outside; and a second electrode disposed in a second partial region other than the first partial region, and spaced apart from the first electrode, and encapsulated within the substrate, wherein each of the first electrode and the second electrode is made of hydrogel having electrical conductivity or a soft polymer having electrical conductivity.

3 Claims, 7 Drawing Sheets

WOUND TREATMENT PATCH USING STATIC ELECTRICITY AND METHOD FOR FABRICATING THE PATCH

CROSS REFERENCE TO RELATED APPLICATIONS

This application claims the benefit under 35 USC §119(a) of Korean Patent Application No. 10-2020-0056913 filed on May 13, 2020 in the Korean Intellectual Property Office, the entire disclosure of which is incorporated herein by reference for all purposes.

BACKGROUND

1. Field

The present disclosure relates to a wound treatment patch using static electricity, and relates to a method for fabricating the wound treatment patch using static electricity.

2. Description of Related Art

In general, a wound treatment patch includes a normal patch and a wet patch. When using the general patch, a gauze is attached to a wound area and absorbs wound discharge. The general patch is mainly used for wounds that need simple protection. The wet patch is used when it is necessary to absorb exudate (wound discharge) that is released after a skin is wounded, and to prevent bleeding or loss of body fluid and contamination, and to create a humid environment.

Recently, the wet patch used to prevent scars from being left is mainly used when the skin is damaged or peeled off due to light abrasion, friction, etc. However, the wet patch may not be used for burns or blisters occur, or deep wounds, or infected wounds.

In order to improve the mentioned limitation and problem, pads for wound treatment using electric stimulation have been developed and studied. However, the pad works only when the pad is connected with a power source and a wire such that a DC-type electric field is created around an affected area. Thus, the pad should be connected to an external battery or power source. This may cause inconvenience in daily life of a patient. Further, power consumption is large when the pad works at all times.

A wound treatment patch is attached to a wound area to treats wounds such as cuts. In general, the patch blocks external bacteria or viruses and prevents deterioration of the wound, thereby helping wound healing. Recently, development of wound treatment patches containing drugs therein leads to high wound treatment efficiency. In order to improve the above-mentioned problems, development of an electric stimulation pad for wound treatment using electric stimulation has been made. However, the electric stimulation pad may not meet requirement of continuous treatment due to the mentioned limitations.

SUMMARY

This Summary is provided to introduce a selection of concepts in a simplified form that are further described below in the Detailed Description. This Summary is not intended to identify all key features or essential features of the claimed subject matter, nor is it intended to be used alone as an aid in determining the scope of the claimed subject matter.

One purpose of the present disclosure is to manufacture a wound treatment patch that is based on body static electricity and thus is used regardless of a wound area and a wound type and without a power source.

Another purpose of the present disclosure is to provide a body static electricity based wound treatment patch that may always work using static electricity induced in the body via electromagnetic waves generated from surrounding electronic devices and body static electricity generated via contact between the body and the surrounding environment, thereby to improve a treatment speed of the affected area and the convenience of the patient.

Purposes of the present disclosure are not limited to the above-mentioned purpose. Other purposes and advantages of the present disclosure as not mentioned above may be understood from following descriptions and more clearly understood from embodiments of the present disclosure. Further, it will be readily appreciated that the purposes and advantages of the present disclosure may be realized by features and combinations thereof as disclosed in the claims.

A first aspect of the present disclosure provides a wound treatment patch using static electricity, the patch comprising: a substrate made of a sticky polymer; a first electrode disposed in a first partial region of one face of the substrate and exposed to an outside; and a second electrode disposed in a second partial region other than the first partial region, and spaced apart from the first electrode, and encapsulated within the substrate, wherein each of the first electrode and the second electrode is made of hydrogel having electrical conductivity or a soft polymer having electrical conductivity.

In one implementation of the first aspect, when the patch is attached to an wound area of a skin, the first electrode connects to the skin acting as a resistor, while the second electrode, the substrate portion between the second electrode and the skin, and the skin as a further electrode constitute a capacitor, such that a difference between current phases of the first and second electrodes occurs, thereby to generate an electric field therebetween to apply electrical stimulation to the wound area.

In one implementation of the first aspect, the difference between current phases of the first and second electrodes generates alternating current (AC) electric field.

A second aspect of the present disclosure provides a method for treating a wound, the method comprising: preparing the wound treatment patch using static electricity as defined above; and attaching the wound treatment patch to a wound area such that the wound area is located between the first and second electrodes of the wound treatment patch.

A third aspect of the present disclosure provides a method for fabricating a wound treatment patch using static electricity, the method comprising: putting a first solution including a sticky polymer material solution into a mold and hardening the first solution to prepare a substrate such that the substrate has two grooves defined in one face thereof having different depths; removing the substrate from the mold; putting a second solution into the two grooves of the substrate such that a first groove of the two grooves is not fully filled with the second solution, and hardening the second solution, wherein the second solution includes a hydrogel solution having electrical conductivity or a soft polymer solution having electrical conductivity; and fully filling the first groove with a third solution including a sticky polymer material solution and hardening the third solution such that a cured product of the second solution is encapsulated in the substrate.

In one implementation of the third aspect, the method further comprises preforming UV treatment on the substrate before putting the second solution such that adhesion between the substrate and the hydrogel having electrical conductivity or the soft polymer having electrical conductivity is improved.

In one implementation of the third aspect, the method further comprises, before putting the second solution, treating the substrate removed from the mold with bnenzophenone to improve adhesion of the substrate to the hydrogel with electrical conductivity or the soft polymer with electrical conductivity.

In one implementation of the third aspect, the first groove is one of the two grooves having a greater depth than a depth of the other thereof.

A fourth aspect of the present disclosure provides a wound treatment patch using static electricity fabricated by the method defined above.

Effects in accordance with the present disclosure may be as follows but may not be limited thereto.

The body static electricity based wound treatment patch according to the present disclosure may always work using static electricity induced in the body via electromagnetic waves generated from surrounding electronic devices and body static electricity generated via contact between the body and the surrounding environment. The body static electricity based wound treatment patch may induce electric charges in the conductive hydrogel using the body static electricity to apply an AC type electric field to the affected area to accelerate wound treatment. Thus, the body static electricity based wound treatment patch does not require an external power source and may work at all times without being constrained by the environment. Thus, the patient's convenience may be dramatically improved compared to the conventional wound treatment pads using the electric field.

BRIEF DESCRIPTIONS OF DRAWINGS

DETAILED DESCRIPTIONS

Figure 1:
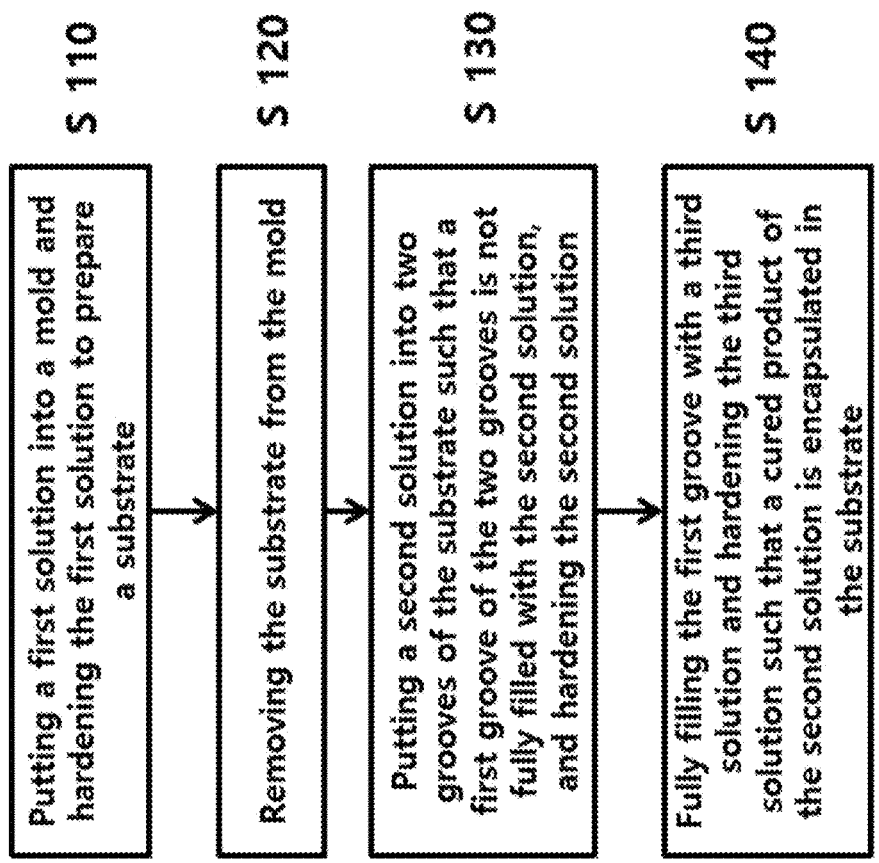
FIG. 1 shows a flow chart of a method for fabricating a wound treatment patch using static electricity according to an embodiment of the present disclosure.

For simplicity and clarity of illustration, elements in the figures are not necessarily drawn to scale. The same reference numbers in different figures represent the same or similar elements, and as such perform similar functionality. Further, descriptions and details of well-known steps and elements are omitted for simplicity of the description. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Examples of various embodiments are illustrated and described further below. It will be understood that the description herein is not intended to limit the claims to the specific embodiments described. On the contrary, it is intended to cover alternatives, modifications, and equivalents as may be included within the spirit and scope of the present disclosure as defined by the appended claims.

The terminology used herein is for the purpose of describing particular embodiments only and is not intended to limit the present disclosure. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or more other features, integers, operations, elements, components, and/or portions thereof. As used herein, the term "and/or" includes any and all combinations of one or more of the associated listed items. Expression such as "at least one of" when preceding a list of elements may modify the entire list of elements and may not modify the individual elements of the list.

It will be understood that, although the terms "first", "second", "third", and so on may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present disclosure.

In addition, it will also be understood that when a first element or layer is referred to as being present "on" or "beneath" a second element or layer, the first element may be disposed directly on or beneath the second element or may be disposed indirectly on or beneath the second element with a third element or layer being disposed between the first and second elements or layers.

It will be understood that when an element or layer is referred to as being "connected to", or "coupled to" another element or layer, it may be directly on, connected to, or coupled to the other element or layer, or one or more intervening elements or layers may be present. In addition, it will also be understood that when an element or layer is referred to as being "between" two elements or layers, it may be the only element or layer between the two elements or layers, or one or more intervening elements or layers may also be present.

Further, as used herein, when a layer, film, region, plate, or the like is disposed "on" or "on a top" of another layer, film, region, plate, or the like, the former may directly contact the latter or still another layer, film, region, plate, or the like may be disposed between the former and the latter. As used herein, when a layer, film, region, plate, or the like is directly disposed "on" or "on a top" of another layer, film, region, plate, or the like, the former directly contacts the latter and still another layer, film, region, plate, or the like is not disposed between the former and the latter. Further, as used herein, when a layer, film, region, plate, or the like is disposed "below" or "under" another layer, film, region, plate, or the like, the former may directly contact the latter or still another layer, film, region, plate, or the like may be disposed between the former and the latter. As used herein, when a layer, film, region, plate, or the like is directly disposed "below" or "under" another layer, film, region, plate, or the like, the former directly contacts the latter and still another layer, film, region, plate, or the like is not disposed between the former and the latter.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As used herein, the body static electricity generally refers to continuous accumulation in the body of (1) electrical charges caused by electromagnetic fields generated by nearby electronic devices and (2) electrical charges induced by friction between the body (mainly, feet) and the environment (mainly, a floor). The wound treatment using an electric field may include applying an external electric field to a body electric field of 70 mV/mm level that occurs naturally in the affected area, thereby enhancing cell regeneration in the affected area and enhancing a healing speed of the wound.

The wound treatment patch using static electricity according to the present disclosure has a special electrode structure to enhance the body static electricity as naturally generated, and thus a stimulating effect on the wound, such that the wound treatment is more effectively achieved.

Figure 2:
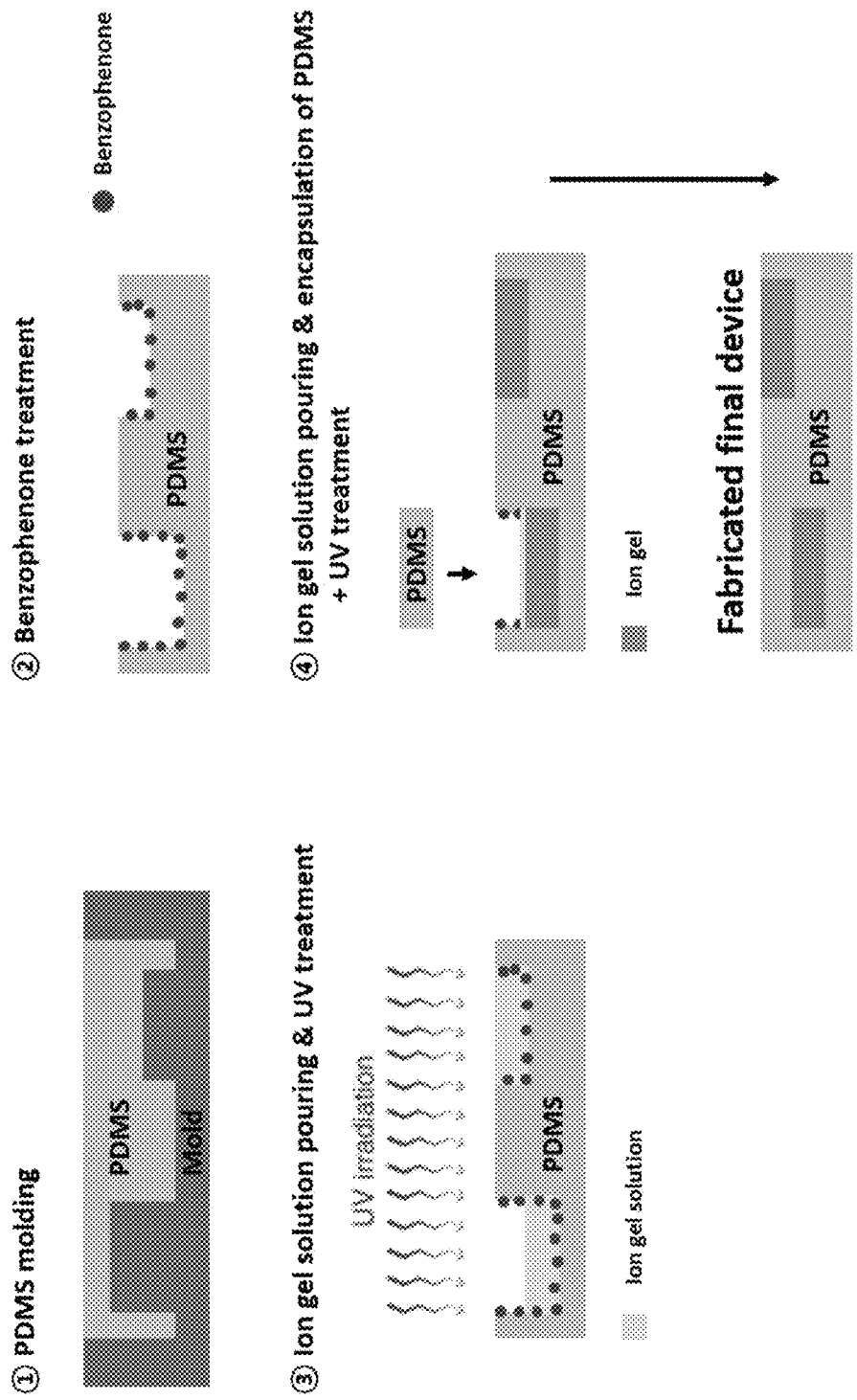
FIG. 2 shows a schematic diagram of a method for fabricating a wound treatment patch using static electricity according to an embodiment of the present disclosure.

FIG. 1 shows a flow chart of a method for fabricating a wound treatment patch using static electricity according to an embodiment of the present disclosure. FIG. 2 shows a schematic diagram of a method for fabricating a wound treatment patch using static electricity according to an embodiment of the present disclosure.

A method for fabricating a wound treatment patch using static electricity according to an embodiment of the present disclosure may include (1) putting a first solution including a sticky polymer material solution into a mold and hardening the first solution to prepare a substrate such that the substrate has two grooves defined in one face thereof having different depths (S 110); (2) removing the substrate from the mold (S 120); (3) putting a second solution into the two grooves of the substrate such that a first groove of the two grooves is not fully filled with the second solution, and hardening the second solution, wherein the second solution includes a hydrogel solution having electrical conductivity or a soft polymer solution having electrical conductivity (S 130); and (4) fully filling the first groove with a third solution including a sticky polymer material solution and hardening the third solution such that a cured product of the second solution is encapsulated in the substrate (S 140).

A method for fabricating a wound treatment patch using static electricity according to an embodiment of the present disclosure may include (1) putting a first solution including a sticky polymer material solution into a mold and hardening the first solution to prepare a substrate such that the substrate has two grooves defined in one face thereof having different depths (S 110).

The first solution may include the sticky polymer material solution. In this connection, the sticky polymer material may include polydimethylsiloxane (PDMS), silbione, a soft non-conductor material coated with an adhesive tape, etc.

The mold has a predefined shape. As shown in FIG. 2, the mold is shaped such that the substrate formed after the molding has two grooves defined in one face thereof having different depths. The mold may be made of material such as PTFE. However, the present disclosure is not limited thereto. These two grooves correspond to positions where two electrodes are placed in a subsequent process.

A method for fabricating a wound treatment patch using static electricity according to an embodiment of the present disclosure may include (1) removing the substrate from the mold (S 120).

The substrate removed from the mold may be treated with bnenzophenone to improve adhesion of the substrate to hydrogel with electrical conductivity or a soft polymer with electrical conductivity. Specifically, it is preferable to treat the substrate using 10% benzophenone for about 5 minutes. Accordingly, it is possible to improve the adhesion between the non-conductive polymer as the substrate material and the conductive hydrogel or the conductive soft polymer.

A method for fabricating a wound treatment patch using static electricity according to an embodiment of the present disclosure may include (3) putting a second solution into the two grooves of the substrate such that a first groove of the two grooves is not fully filled with the second solution, and hardening the second solution, wherein the second solution includes a hydrogel solution having electrical conductivity or a soft polymer solution having electrical conductivity (S 130).

Why the first groove of the two grooves is not fully filled with the second solution is as follows. The wound treatment patch according to the present disclosure has two electrodes. One electrode directly contacts a skin to form resistor connection thereto, and the other electrode does not directly contact the skin to forms capacitor connection thereto. Therefore, one of the two grooves, that is, the first groove must not be fully filled with the second solution to form an second electrode that does not directly contact the skin. Preferably, the first groove may have a greater depth than that of a second groove.

The material used as the electrode may include hydrogel having electrical conductivity or soft polymer having electrical conductivity. Examples thereof may include PAAm (polyacrylamide), PDA (polydopamine), PDA-copolymer or hydrogel or soft polymer having electrical conductivity containing NaCl, LiCl, AgNW, or the like.

Further, in (3), the adhesion between the substrate material and the hydrogel having electrical conductivity or the soft polymer having electrical conductivity is improved via UV treatment.

A method for fabricating a wound treatment patch using static electricity according to an embodiment of the present disclosure may include (4) fully filling the first groove with a third solution including a sticky polymer material solution and hardening the third solution such that a cured product of the second solution is encapsulated in the substrate (S 140). In this way, the wound treatment patch using static electricity according to an embodiment of the present disclosure may be completed. This patch is shown in FIG. 2.

Figure 3:
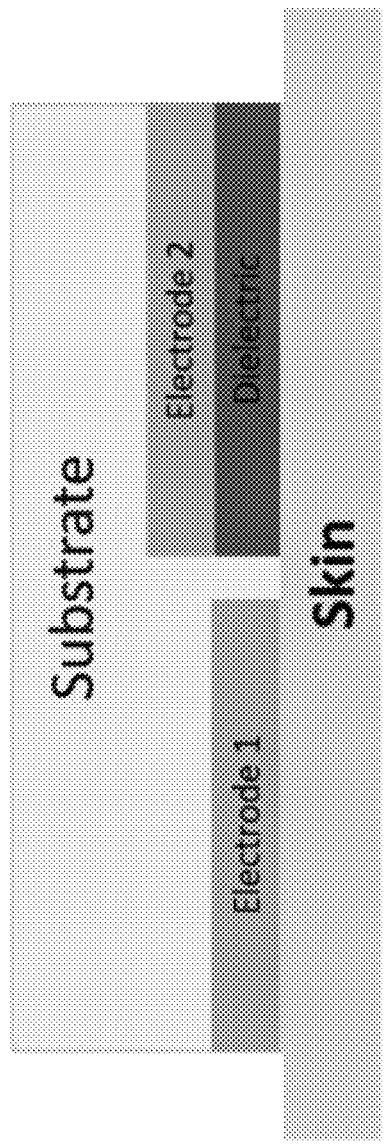
FIG. 3 shows a cross-sectional view of a wound treatment patch using static electricity according to an embodiment of the present disclosure.

A final structure of the wound treatment patch using the static electricity as fabricated via S 110 to S 140 may be identified in FIG. 3.

FIG. 3 shows a cross-sectional view of a wound treatment patch using static electricity according to an embodiment of the present disclosure.

As shown in FIG. 3, the wound treatment patch using static electricity according to an embodiment of the present disclosure includes a substrate (Substrate) made of a sticky polymer; a first electrode (Electrode 1) disposed in a first partial region of one face of the substrate and exposed to an outside; and a second electrode (Electrode 2) disposed in a second partial region other than the first partial region, and spaced apart from the first electrode and encapsulated within the substrate.

Figure 4:
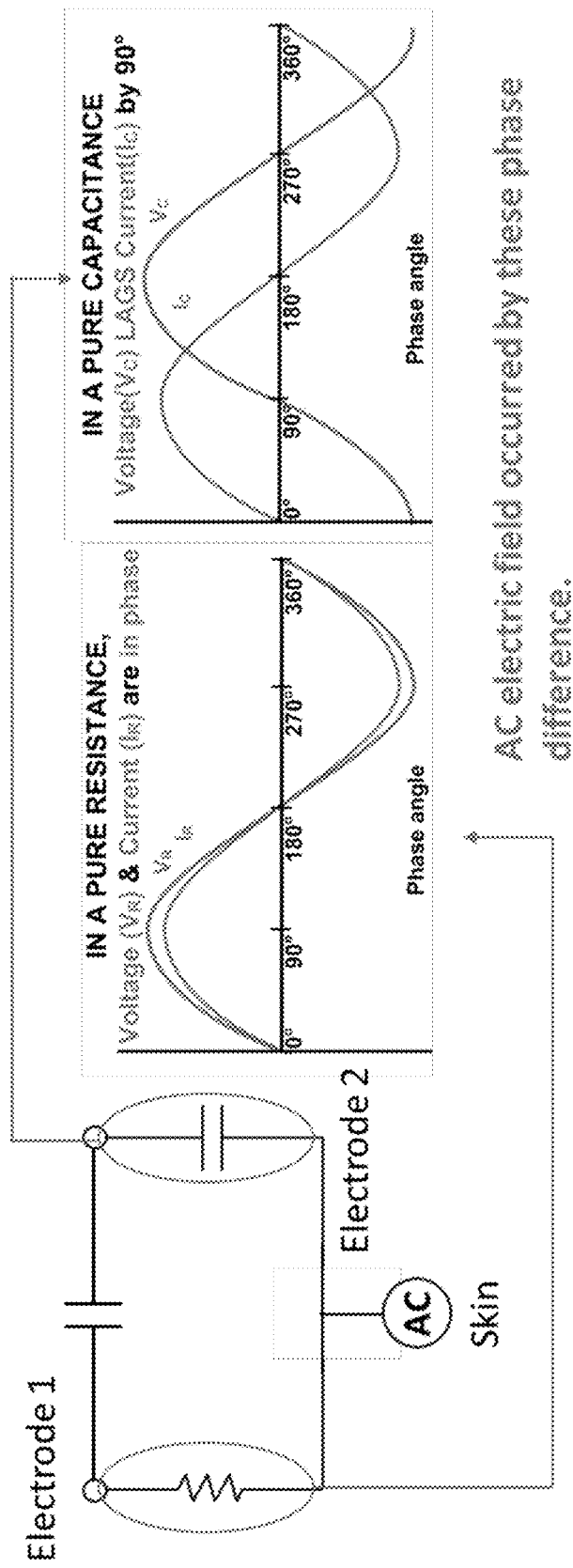
FIG. 4 is a diagram of a working principle of a wound treatment patch based on body static electricity.

In according to the present disclosure, as shown in FIG. 3, the two electrodes are arranged such that one electrode (Electrode 1) contacts the skin and the other electrode (Electrode 2) does not contact the skin. The first electrode (Electrode 1) in contact with the skin has resistor connection thereto while the skin acts as a resistor. The second electrode (Electrode 2) which does not come into contact with the skin has capacitor connection thereto while the skin acts as an electrode. In this way, the first electrode is connected to the resistor as the skin, while the second electrode is connected to the skin via the substrate material as dielectric such that the second electrode, the substrate material, and the skin constitute a capacitor. Thus, as shown in FIG. 4, a phase difference or a signal delay may occur between the first and second electrodes. As a result, an electric field is generated between the first and second electrodes. In other words, when the patch is attached to the wound site, the first electrode connects to the resistor and the second electrode constitutes the capacitor together with the skin. Thus, the signal delay or the phase difference may occur between the first and second electrodes such that the electric field is generated between the first and second electrodes. The electric field applies electrical stimulation to the wound.

FIG. 4 is a diagram of a working principle of a wound treatment patch based on body static electricity. As shown in FIG. 4, an electric field is generated due to a signal delay between the two electrodes due to the electrical circuit difference between the two electrodes. That is, an AC electric field is generated due to the phase difference between the two electrodes.

Figure 5:
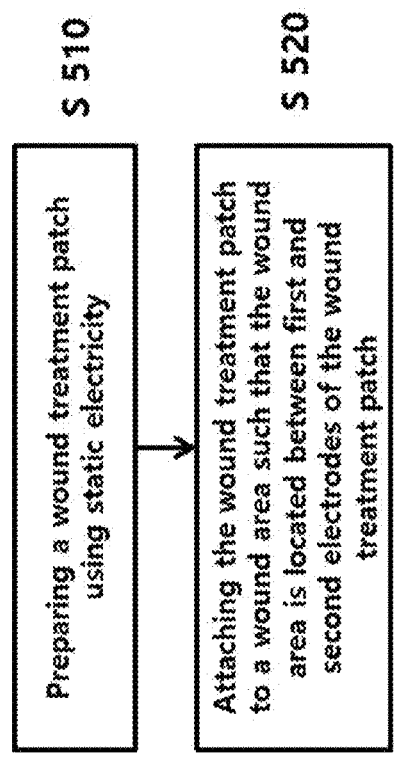
FIG. 5 shows a flowchart of a method for attaching a wound treatment patch using static electricity according to an embodiment of the present disclosure.

FIG. 5 shows a flowchart of a method of attaching a wound treatment patch using static electricity according to an embodiment of the present disclosure.

As shown in FIG. 5, a method of attaching a wound treatment patch using static electricity according to an embodiment of the present disclosure includes preparing a wound treatment patch using static electricity according to the present disclosure (S 510); and attaching the wound treatment patch using the static electricity to a wound area (S 520).

Figure 6:
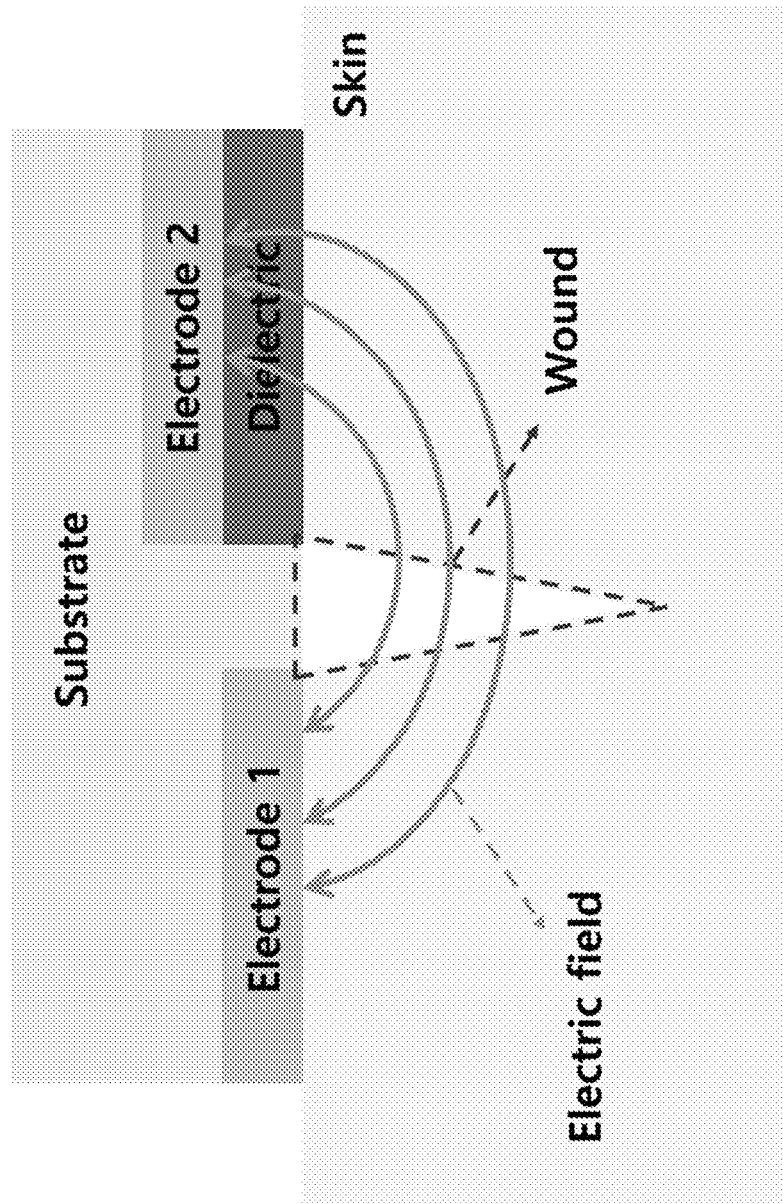
FIG. 6 shows a state in which a wound treatment patch using static electricity according to an embodiment of the present disclosure is attached to a wound site.
Figure 7:
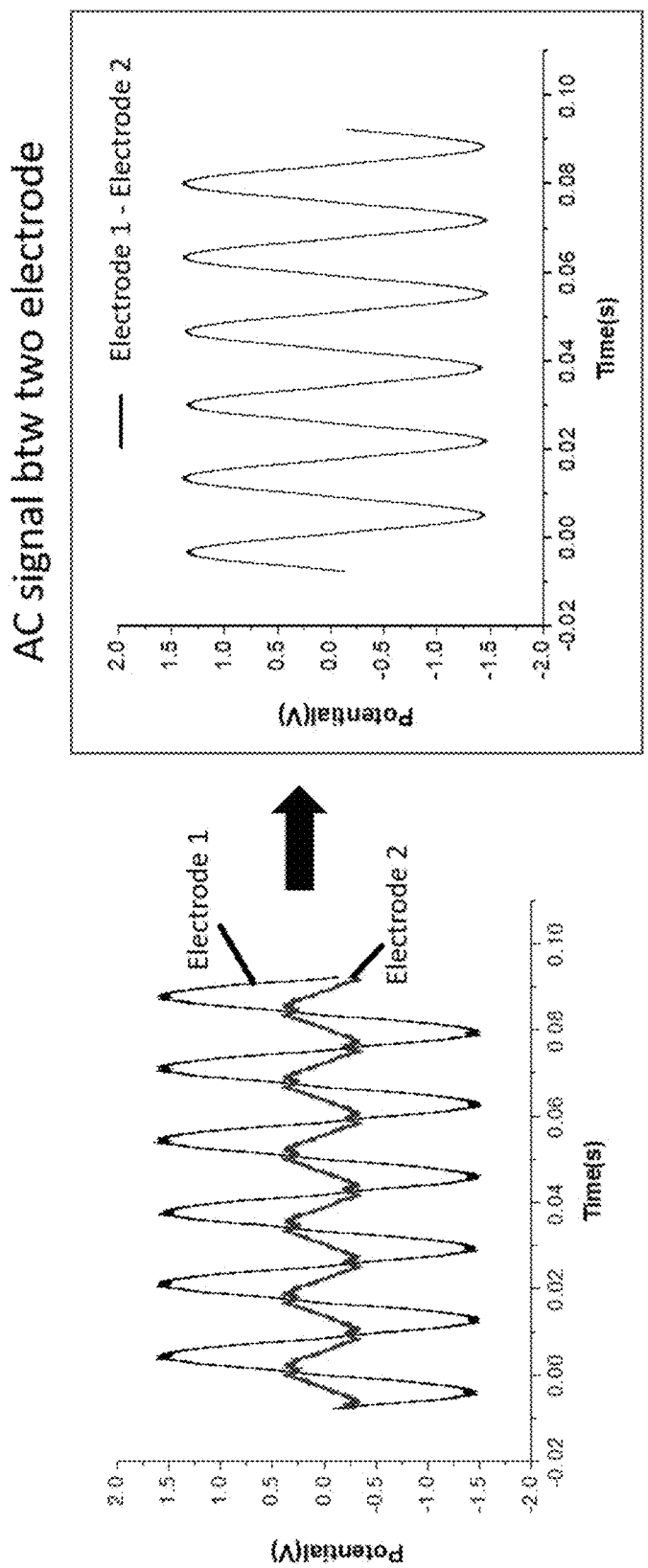
FIG. 7 shows an output measurement result using an oscilloscope when a wound treatment patch using static electricity according to an embodiment of the present disclosure is attached to a wound area.

In this case, it is desirable that the wound site is located between the two electrodes of the wound treatment patch using the static electricity. It is most efficient in terms of the wound treatment when the wound site disposed between the electrodes. Alternatively, the wound may be disposed beneath the electrodes. In other words, although it may suffice that the wound site is located only in a region where the electric field is present, it is most efficient in terms of the wound treatment when the wound site disposed between the electrodes because the effect of electric field amplification is highest when the wound site is located between the two electrodes. This may be identified in FIG. 6. FIG. 6 shows a state in which a wound treatment patch using static electricity is attached to a wound site according to an embodiment of the present disclosure. Further, FIG. 7 shows the result of an output measurement using an oscilloscope when a wound treatment patch using static electricity according to the present disclosure is attached to a wound area.

Hereinafter, the present disclosure will be additionally described based on specific Examples.

EXAMPLE 1

Polydimethylsiloxane (PDMS) was used as a substrate material. Polyacrylamide (PAAm) hydrogel was used as an electrode material. Thus, the patch was fabricated. In order to identify actual workability of the patch, a potential difference generated in the patch was measured. An oscilloscope was used to measure the potential difference.

The specific manufacturing process of the patch is shown in FIG. 2. The final completed patch is shown in FIG. 3.

Step 1: A liquid substrate material (PDMS polymer material) was put into a PTFE mold and was hardened. In this connection, the mold had two grooves having different depths.

Step 2: The hardened polymer was removed from the mold and was treated with 10% benzophenone for 5 minutes on a region thereof to which the conductive hydrogel will be adhered. This process plays a role of enhancing a bonding force between the conductive polymer and a Si based non-conductive polymer such as PDMS.

Step 3: The conductive hydrogel solution (polyacrylamide (PAAm) hydrogel) was put into the two grooves defined in the substrate that has been treated with Benzophenone, and then was hardened. In this connection, one of the two grooves was not fully filled with the solution. In this case, the adhesion between the benzophenone-treated silicone-based non-conductive polymer and the conductive polymer was improved via UV treatment of the polyacrylamide (PAAm) hydrogel.

Step 4: PDMS or Silbione solution was put onto a top face of the conductive hydrogel which was contained in the groove was not completely filled with the solution in Step 3. Then, the filled solution was hardened.

FIG. 7 shows the result of measuring the output via an oscilloscope after the actual patch is manufactured. It was identified based on FIG. 7 that a potential difference of about 3V occurred between the two ion gel based electrodes. The measurement environment was set such that voltage outputs generated at the two electrodes of the patch were measured at the same time while the body was fixed and a power source was not connected to the patch.

As described above, the present disclosure is described with reference to the drawings. However, the present disclosure is not limited to the embodiments and drawings disclosed in the present specification. It will be apparent that various modifications may be made thereto by those skilled in the art within the scope of the present disclosure. Furthermore, although the effect resulting from the features of the present disclosure has not been explicitly described in the description of the embodiments of the present disclosure, it is obvious that a predictable effect resulting from the features of the present disclosure should be recognized.

What is claimed is:

1. A wound treatment patch using a body static electricity, the patch comprising:
   a substrate made of a sticky polymer;

a first electrode disposed in a first partial region of one face of the substrate and exposed to an outside, such that the first electrode is arranged to directly contact a skin to form a resistive connection to the skin; and a second electrode disposed in a second partial region other than the first partial region, electrically isolated from the first electrode, and encapsulated within the substrate, such that the second electrode is arranged to not directly contact the skin to form a capacitive connection to the skin, wherein each of the first electrode and the second electrode is made of hydrogel having electrical conductivity or a soft polymer having electrical conductivity, and wherein in response to the patch being attached to a wound area of the skin, the first electrode connects to the skin acting as a resistor, while the second electrode, the substrate portion between the second electrode and the skin, and the skin as a further electrode constitute a capacitor, such that the wound treatment patch is configured to use the body static electricity induced in a body and apply an electric field generated by a phase difference between the first electrode and the second electrode to the wound area.

2. The wound treatment patch of claim 1, wherein the phase difference between the first and second electrodes generates alternating current (AC) electric field.

3. A method for treating a wound, the method comprising:
preparing a wound treatment patch based on a body static electricity, the wound treatment patch comprising:

a substrate made of a sticky polymer;

a first electrode disposed in a first partial region of one face of the substrate and exposed to an outside, such that the first electrode is arranged to directly contact a skin to form a resistive connection to the skin; and a second electrode disposed in a second partial region other than the first partial region, electrically isolated from the first electrode, and encapsulated within the substrate, such that the second electrode is arranged to not directly contact the skin to form a capacitive connection to the skin; and attaching the wound treatment patch to a wound area such that the wound area is located between the first and second electrodes of the wound treatment patch, wherein each of the first and second electrodes is made of hydrogel having electrical conductivity or a soft polymer having electrical conductivity, and wherein in response to the patch being attached to a wound area of the skin, the first electrode connects to the skin acting as a resistor, while the second electrode, the substrate portion between the second electrode and the skin, and the skin as a further electrode constitute a capacitor, such that the wound treatment patch is configured to use the body static electricity induced in a body and apply an electric field generated by a phase difference between the first electrode and the second electrode to the wound area.

* * * * *